United States Patent
Srivastava et al.

(10) Patent No.: US 10,736,821 B2
(45) Date of Patent: Aug. 11, 2020

(54) PREPARATION AND USE OF SILVER SULFADIAZINE-IMMOBILIZED FILLERS

(71) Applicant: University of Massachusetts, Boston, MA (US)

(72) Inventors: Rohit Srivastava, Lowell, MA (US); Yuyu Sun, Acton, MA (US)

(73) Assignee: University of Massachusetts, Boston, MA (US)

( * ) Notice: Subject to any disclaimer, the term of this patent is extended or adjusted under 35 U.S.C. 154(b) by 154 days.

(21) Appl. No.: 15/571,491

(22) PCT Filed: May 18, 2016

(86) PCT No.: PCT/US2016/032938
§ 371 (c)(1),
(2) Date: Nov. 2, 2017

(87) PCT Pub. No.: WO2016/187236
PCT Pub. Date: Nov. 24, 2016

(65) Prior Publication Data
US 2018/0125763 A1 May 10, 2018

Related U.S. Application Data

(60) Provisional application No. 62/164,844, filed on May 21, 2015.

(51) Int. Cl.
*A61K 6/54* (2020.01)
*C03C 17/28* (2006.01)
*A61K 6/69* (2020.01)
*A61K 6/71* (2020.01)
*A61K 6/844* (2020.01)
*C07C 311/44* (2006.01)
*C07D 239/18* (2006.01)
(Continued)

(52) U.S. Cl.
CPC .................. *A61K 6/54* (2020.01); *A61K 6/69* (2020.01); *A61K 6/71* (2020.01); *A61K 6/844* (2020.01); *C03C 17/28* (2013.01); *C07C 311/44* (2013.01); *C07D 239/18* (2013.01); *C07D 251/28* (2013.01); *C07F 1/10* (2013.01); *C01D 7/00* (2013.01); *C03C 2201/54* (2013.01); *G01N 2021/3595* (2013.01); *G01N 2223/418* (2013.01)

(58) Field of Classification Search
None
See application file for complete search history.

(56) References Cited

U.S. PATENT DOCUMENTS 3,198,641 A * 8/1965 Searight .................... C03C 3/14
501/34
5,852,015 A * 12/1998 Gluzman ............. C07D 251/44
514/245
(Continued)

FOREIGN PATENT DOCUMENTS

WO   WO-2008096918 A1 * 8/2008 ............. A01N 43/66

*Primary Examiner* — Bethany P Barham
*Assistant Examiner* — Barbara S Frazier
(74) *Attorney, Agent, or Firm* — Milstein Zhang & Wu LLC

(57) ABSTRACT

Silver sulfadiazine-immobilized inorganic fillers are described, and their synthesis is presented. The fillers are believed to have utility in dental composites and dental adhesives to achieve potent, long-term, and none-leaching antimicrobial effects.

3 Claims, 7 Drawing Sheets

(51) Int. Cl.
*C07D 251/28* (2006.01)
*C07F 1/10* (2006.01)
C01D 7/00 (2006.01)
G01N 21/35 (2014.01)

(56) References Cited

U.S. PATENT DOCUMENTS

| | | | | |
|---|---|---|---|---|
| 7,863,058 B2* | 1/2011 | Zhao | ................... | C07D 251/12 |
| | | | | 435/6.12 |
| 2013/0158157 A1* | 6/2013 | Stelzig | ................ | A61K 6/0008 |
| | | | | 523/116 |

* cited by examiner

PREPARATION AND USE OF SILVER SULFADIAZINE-IMMOBILIZED FILLERS

CROSS-REFERENCE TO RELATED APPLICATIONS

This application is the U.S. national phase of and claims priority to PCT/US16/32938, filed May 18, 2016, which claims the benefit of priority to U.S. Provisional Application Ser. No. 62/164,844, filed on May 15, 2015, the entire content of each of which is incorporated herein by reference for all purposes.

FIELD OF THE INVENTION

The invention relates to antimicrobial compositions of matter in general and particularly to a composition of matter that employs silver metal ions.

BACKGROUND OF THE INVENTION

Polymer resin/inorganic filler-based composites are widely used as dental restorative materials and dental adhesives. In the US alone billions of dollars are spent in dental filling procedures using such materials every year. However, bacterial adhesion and biofilm-formation on such materials can lead to secondary caries, one of the major causes of the short service life (around several years) of the current resin-based dental restorations.

Three general methods have been tried to introduce antimicrobial functions into dental composites to control microbial adhesion and biofilm formation. The first method is to add monomeric organic antimicrobial agents directly into the composites. However, release of the antimicrobial agents will shorten the antimicrobial duration and deteriorate physical properties of the resulting materials. The second method is to add inorganic nano particles (e.g., silver, titanium dioxide, zinc oxide, etc.) into dental composites. However, the cost to prepare and use the nano particles is high, the complete mixing of the nano particles with the current dental composite formulation is difficult to achieve (e.g., nano particle aggregation occurs), and the potential health risk associated with the processing and use of nano particles is a concern. The third method is to add quaternary ammonium-containing monomers into the formulation to copolymerize with resin monomers. However, the new monomers have misciblity/compatiblity issues with the current resin monomers. In addition, quaternary ammonium salts have weak antimicrobial effects, and the effects can be quenched (stopped) by ionic compounds such as surface-active agents found in normal toothpastes.

In summary, antimicrobial activity is needed in resin-based dental restorative and adhesive materials that can inhibit microbial adhesion and secondary caries so as to prolong the service life of the resins. However, none of the current materials and methods provide a solution to these problems.

SUMMARY OF THE INVENTION

According to one aspect, the invention features a composition of matter, comprising: a particulate substrate comprising an inorganic filler; an amine-terminated hydrocarbon molecule moiety covalently bonded by way of a carbon atom of the hydrocarbon molecule moiety to the inorganic filler; a cyanuric chloride molecule moiety bonded to an amine group of the amine-terminated hydrocarbon molecule moiety; a sulfadiazine molecule moiety bonded to the cyanuric chloride molecule moiety; and a silver metal ion incorporated in the sulfadiazine moiety.

In one embodiment, a second sulfadiazine molecule moiety is bonded to the cyanuric chloride molecule moiety.

In another embodiment, the second sulfadiazine molecule moiety has a second silver metal ion incorporated therein.

In yet another embodiment, the particulate substrate comprising an inorganic filler is a particulate glass substrate.

In still another embodiment, the particulate glass substrate comprises a glass containing BaO.

In a further embodiment, the amine-terminated hydrocarbon molecule moiety is (3-aminopropyl)trimethoxysilane.

According to another aspect, the invention relates to a method of producing a composition of matter, comprising the steps of: providing a particulate substrate comprising an inorganic filler; reacting the inorganic filler with an amine-terminated hydrocarbon molecule moiety to covalently bond the hydrocarbon molecule moiety by way of a carbon atom thereof to the inorganic filler to produce an amine modified substrate; reacting the amine modified substrate with a cyanuric chloride molecule moiety to bond the cyanuric chloride molecule moiety to an amine group of the amine-terminated hydrocarbon molecule moiety to produce an amine modified substrate-CyCl composition; reacting the amine modified substrate-CyCl composition with a sulfadiazine molecule moiety to bond an amine moiety of the sulfadiazine molecule moiety to the cyanuric chloride molecule moiety by displacing a chlorine atom thereof to produce an amine modified substrate-CyCl-SD composition; and reacting the amine modified substrate-CyCl-SD composition with a silver metal ion to incorporate the silver metal ion in the sulfadiazine moiety to produce a silver sulfadiazine-immobilized inorganic filler material.

In one embodiment, the particulate substrate is a particulate glass substrate.

In another embodiment, the step of reacting the inorganic filler with an amine-terminated hydrocarbon molecule moiety is performed using a reaction medium comprising cyclohexane and n-propyl amine.

In yet another embodiment, the step of reacting the amine modified substrate with a cyanuric chloride molecule moiety is performed in a reaction medium comprising $Na_2CO_3$, acetone and water.

In still another embodiment, the step of reacting the amine modified substrate-CyCl composition with a sulfadiazine molecule moiety is performed using DMSO, $Na_2CO_3$ and water.

In a further embodiment, the step of reacting the amine modified substrate-CyCl-SD composition with a silver metal ion is performed in a reaction medium of DI water.

According to another aspect, the invention relates to a method of using a composition of matter, comprising the steps of: providing a composition of matter comprising a silver sulfadiazine-immobilized inorganic filler; mixing the composition of matter comprising a silver sulfadiazine-immobilized inorganic filler with a dental composite or dental adhesive formulation to produce a mixture; and applying the mixture as a replacement material for at least a part of a tooth in a mouth of a patient.

In one embodiment, the silver sulfadiazine-immobilized inorganic filler comprises a particulate glass substrate.

In another embodiment, the particulate glass substrate comprises BaO.

In yet another embodiment, the silver sulfadiazine-immobilized inorganic filler comprises an amine-terminated hydrocarbon molecule moiety.

In still another embodiment, the silver sulfadiazine-immobilized inorganic filler comprises a cyanuric chloride molecule moiety bonded to an amine group of the amine-terminated hydrocarbon molecule moiety.

In a further embodiment, the silver sulfadiazine-immobilized inorganic filler comprises an amine moiety of a sulfadiazine molecule moiety to the cyanuric chloride molecule moiety.

In yet a further embodiment, the silver sulfadiazine-immobilized inorganic filler comprises a silver metal ion incorporated in the sulfadiazine moiety.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

The invention creates silver sulfadiazine-immobilized inorganic fillers, and uses the resulting fillers in dental composites and dental adhesives to achieve potent, long-term, and none-leaching antimicrobial effects. In the examples that follow, glass is recited as a substrate material. It is believed that other biologically-inert inorganic materials may also be used as suitable particulate substrates in place of glass. In various embodiments, the methods of the invention include the following steps:

Sulfadiazine is covalently attached onto conventional inorganic fillers (such as glass powders) used in dental composites. This can be achieved by chemically modifying the filler surfaces to introduce reactive groups onto the filler surfaces, and then reacting the new functional groups with the amino groups on sulfadiazine to form covalent linkage. The resulting sulfadiazine-filler conjugates are believed to be novel. The following examples show how this can be done.

Figure 1:
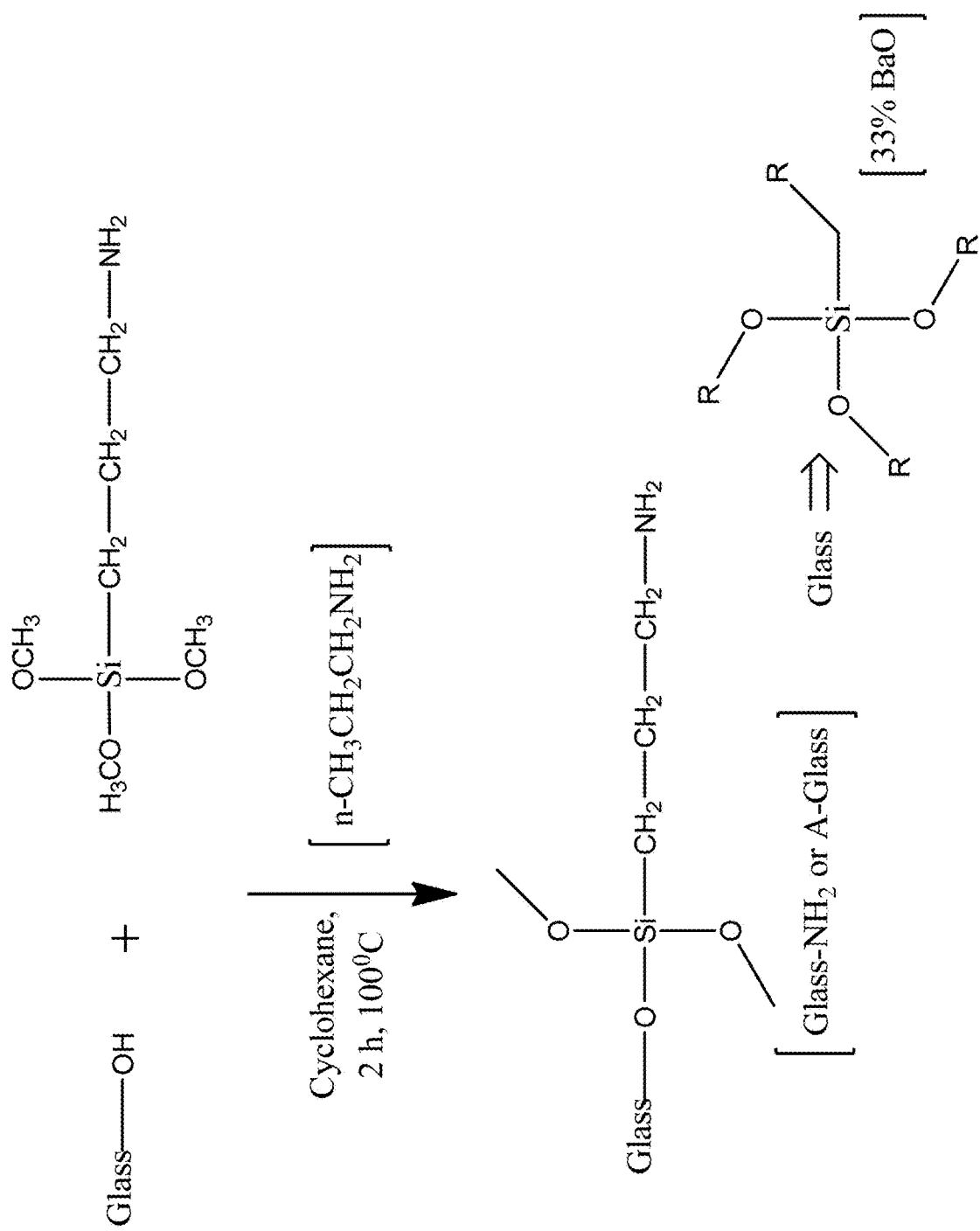
FIG. 1 is a reaction scheme for preparing a glass substrate with (3-aminopropyl)trimethoxysilane (APTMS).

Preparation of Amine Modified Glass (A-Glass):

FIG. 1 is a reaction scheme for preparing a glass substrate with (3-aminopropyl)trimethoxysilane (APTMS). As shown in FIG. 1, in one embodiment 8.0 g glass powder was reacted with 12.0 ml (3-aminopropyl)trimethoxysilane in a reaction medium comprising mixed with 100 ml cyclohexane and 3.2 ml n-propyl amine. The reaction was allowed to proceed at room temperature for 2 h. The solvent was then removed under vacuum and keep the sample in oven at 100° C. for 2 h. The samples were washed with cyclohexane 3 times under ultracentrifugation to remove unattached APTMS and other side products. Finally the sample was dried under vacuum. The glass is illustrated in the lower right corner of FIG. 1 as silicate glass having approximately 33% BaO content. It is believed that the reaction of the (3-aminopropyl)trimethoxysilane with the glass occurs at hydroxyl moieties in the glass surface.

Figure 2:
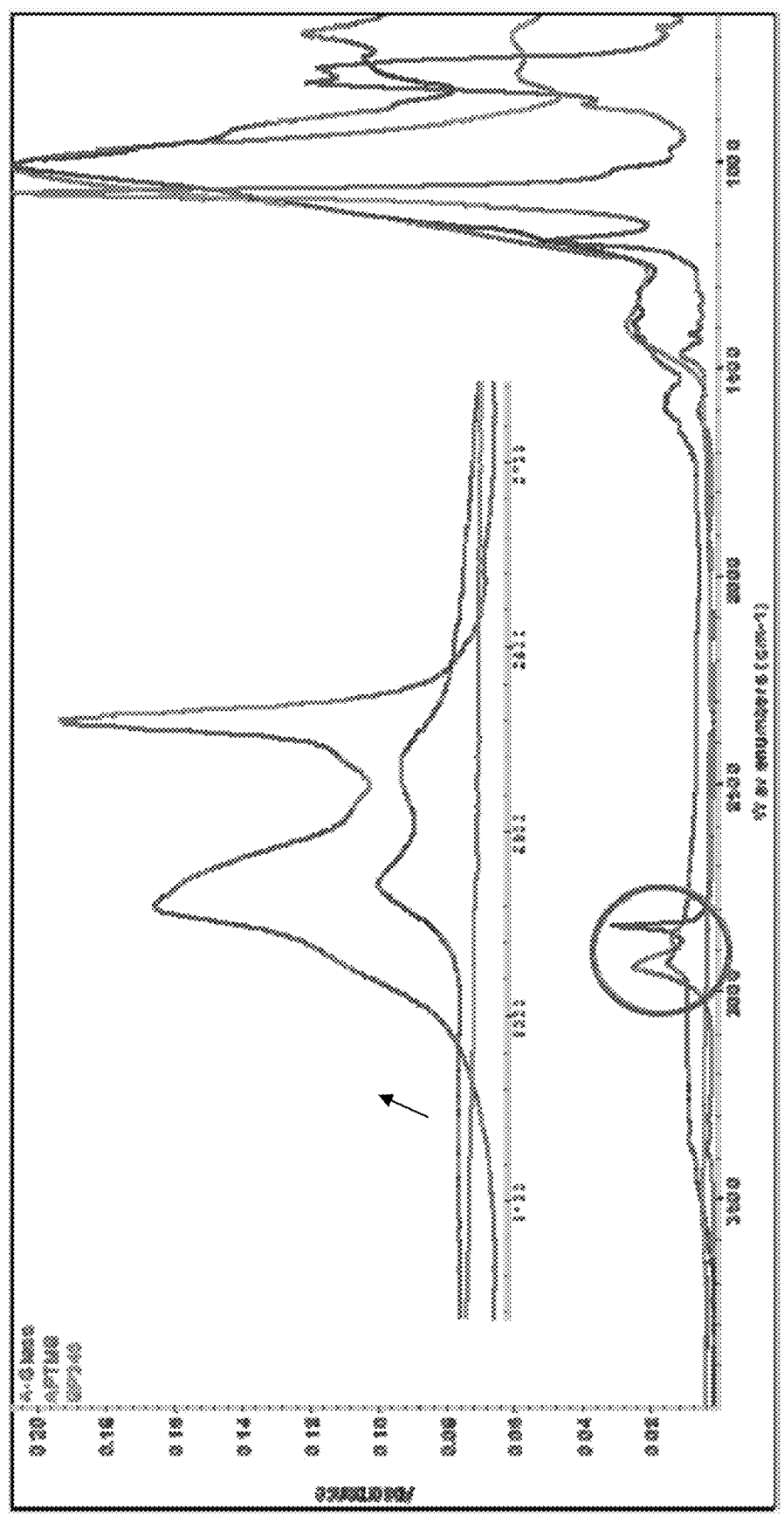
FIG. 2 is an FTIR spectrum of A-Glass, or amine-functionalized glass as produced by the reaction scheme of FIG. 1.

The amine functionalization at the glass surface was confirmed by FTIR as shown in FIG. 2. FIG. 2 is an FTIR spectrum of A-Glass, or amine-functionalized glass as produced by the reaction scheme of FIG. 1.

The Reaction of Cyanuric Chloride with the Amine-Modified Glass to Prepare A-Glass-CyCl Cyanuric chloride is an organic compound with the formula $(NCCl)_3$ and the chemical structure

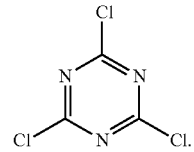

Place 4 g amine modified glass (A-Glass) into a 3-neck round bottom flask. Add 80 ml acetone and stir the solution for 15 min at 0-5° C. After proper dispersion of A-Glass in acetone, add 1.970 g (10.3 m mol) cyanuric chloride. After mixing, add $Na_2CO_3$ solution (1.280 g in 35 ml water), and continue the reaction at 0-5° C. for 1 h and then at 30° C. for 2 h. Wash the product (A-Glass-CyCl) with acetone 3 times and dry it under vacuum.

Reaction of Sulfadiazine with the Cyanuric Chloride Treated Amine Modified Glass (A-Glass-CyCl-SD)

Sulfadiazine is a sulfonamide antibiotic having the chemical structure

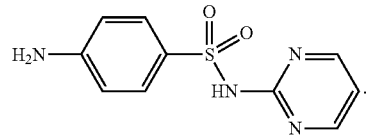 [SMILES: Nc1ccc(S(=O)(=O)Nc2ncccn2)cc1]

3 g of A-Glass-CyCl were added to 80 ml DMSO, and 1.5732 g sulfadiazine (SD) was added, followed by the addition of aqueous $Na_2CO_3$ solution (0.7417 g in 50 ml DI water) dropwise over the period of 30 min. After reaction at 60° C. for 5 h, the temperature was increased to 100° C. for the next 3 h. The reaction was then continued at room temperature overnight. The products were washed with 2 times with DMSO and then 3 times with DI water, and dried under vacuum.

Figure 3:
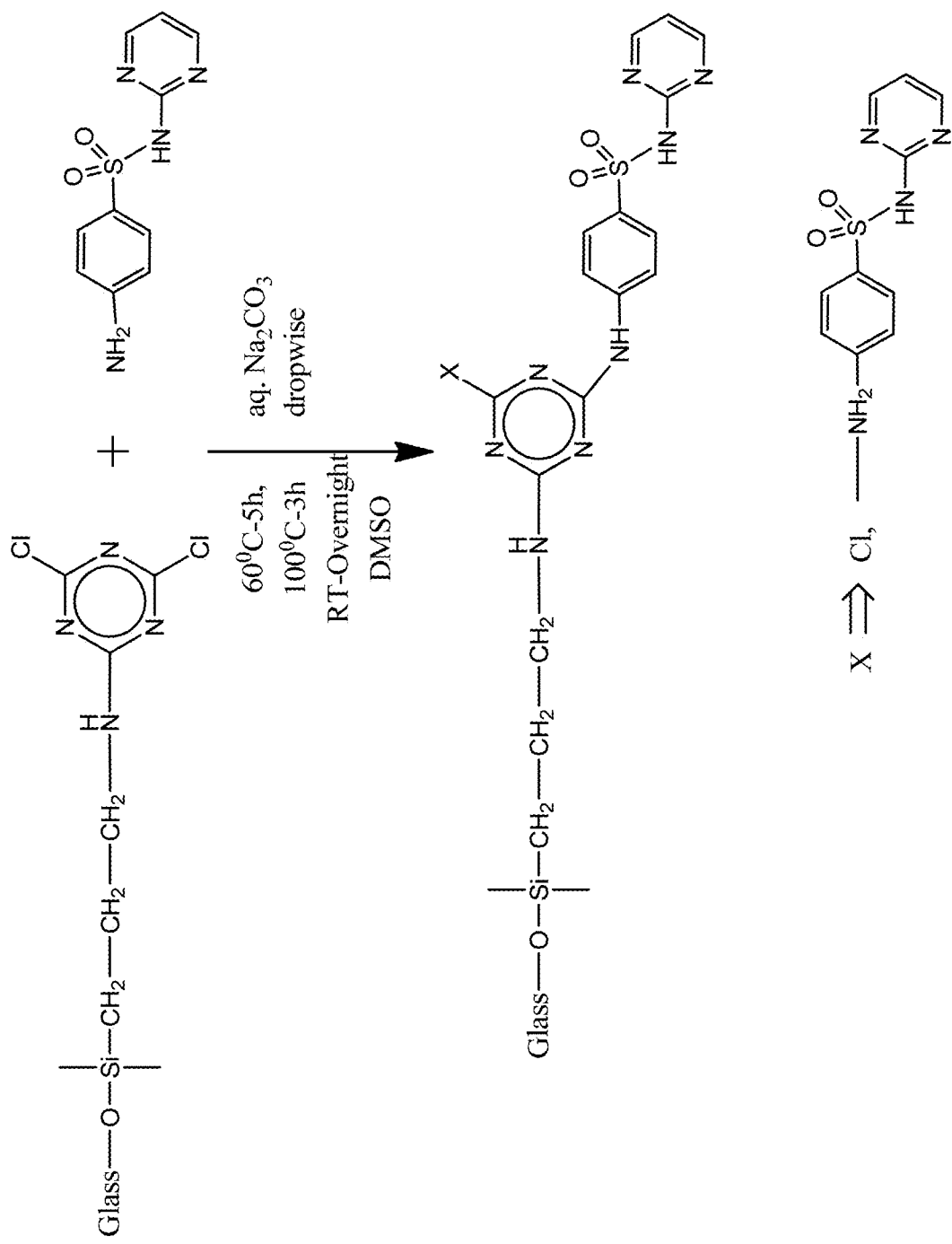
FIG. 3 is a schematic reaction of A-Glass-CyCl with sulfadiazine to produce reaction product A-Glass-CyCl-SD.

FIG. 3 is a schematic reaction of A-Glass-CyCl with sulfadiazine to produce reaction product A-Glass-CyCl-SD.

The reaction product A-Glass-CyCl-SD is confirmed by FTIR analysis and KI test.

Figure 4:
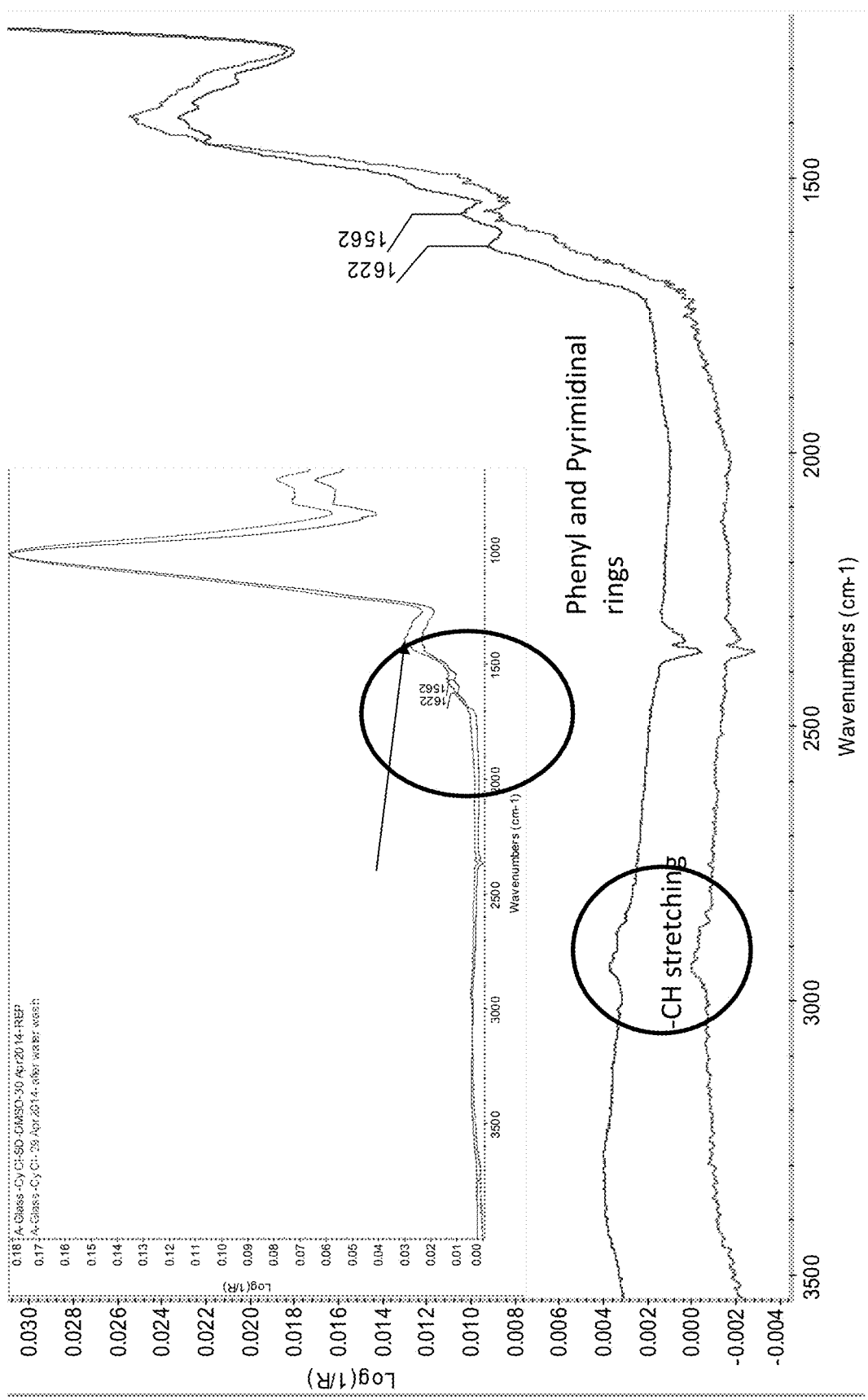
FIG. 4 is an FTIR spectrum of A-Glass-CyCl-SD.

FIG. 4 is an FTIR spectrum of A-Glass-CyCl-SD.

The KI Test

Treat a small amount of modified glass powder A-Glass-CyCl-SD with 1:30 dilute chlorine bleach at room temperature (RT) for 1 h. After treatment, filter it and wash with DI water thoroughly to remove unreacted chlorine bleach. Dry the powder at RT and treat it with 5% aqueous solution of KI. There is a color change from white to yellow-brown spontaneously as shown in FIG. 5A and FIG. 5B.

Figures 5A, 5B:
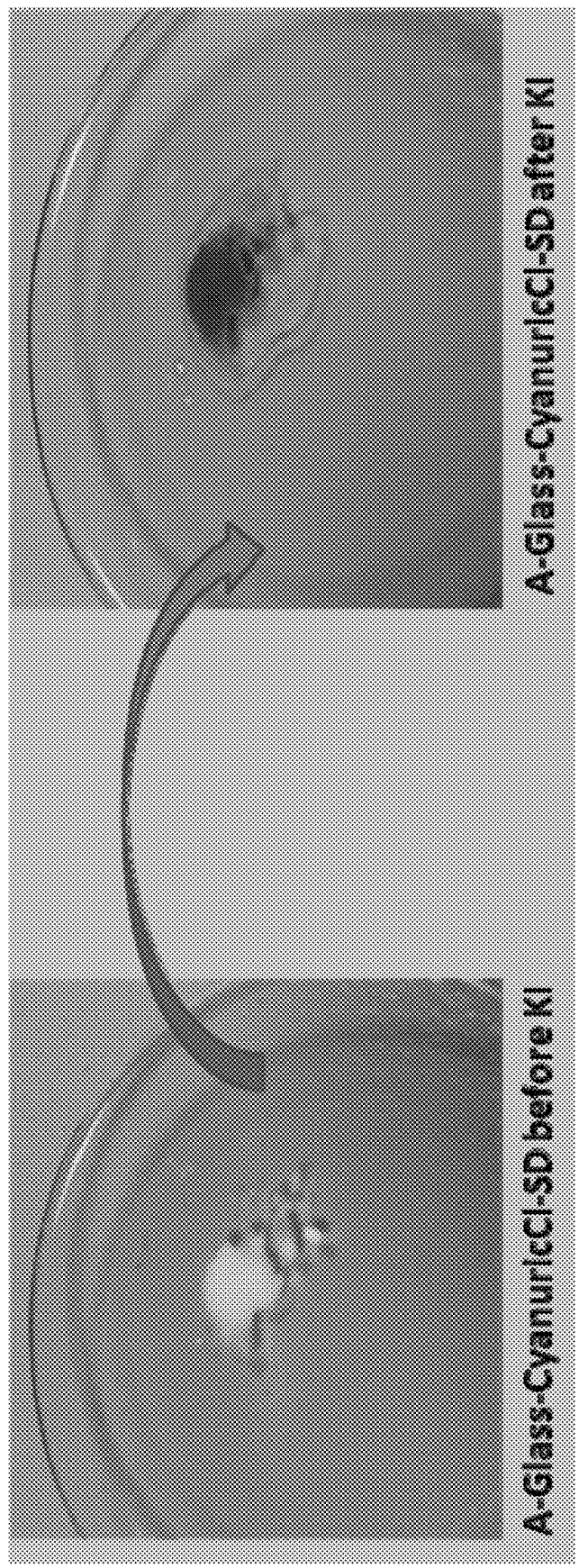
FIG. 5A is an image of A-Glass-CyCl-SD treated with chlorine bleach.
FIG. 5B is an image of A-Glass-CyCl-SD treated with chlorine bleach and then with KI.

FIG. 5A is an image of A-Glass-CyCl-SD treated with chlorine bleach.

FIG. 5B is an image of A-Glass-CyCl-SD treated with chlorine bleach and then with KI.

Preparation of Silver Sulfadiazine-Inorganic Filler Conjugates

Silver sulfadiazine-inorganic filler conjugates are prepared. This is accomplished by reacting sulfadiazine-filler conjugates as described above with a source that can provide silver, e.g., silver nitrate aqueous solution. The sulfadiazine will form a complex with the silver cations, leading to the formation of silver sulfadiazine-inorganic filler conjugates, which are believed never to have been reported before. The following example shows how this can be done.

Silver Salt of Modified Glass (A-Glass-CyCl-SD-Ag)

Put 2.5 g of A-Glass-CyCl-SD in 60 ml DI water in a small beaker under magnetic stirring. Add 0.65 g $AgNO_3$, and stir the mixture at room temperature under dark overnight. After the reaction, wash the sample with DI water 6 times to remove un-attached silver.

Figure 6:
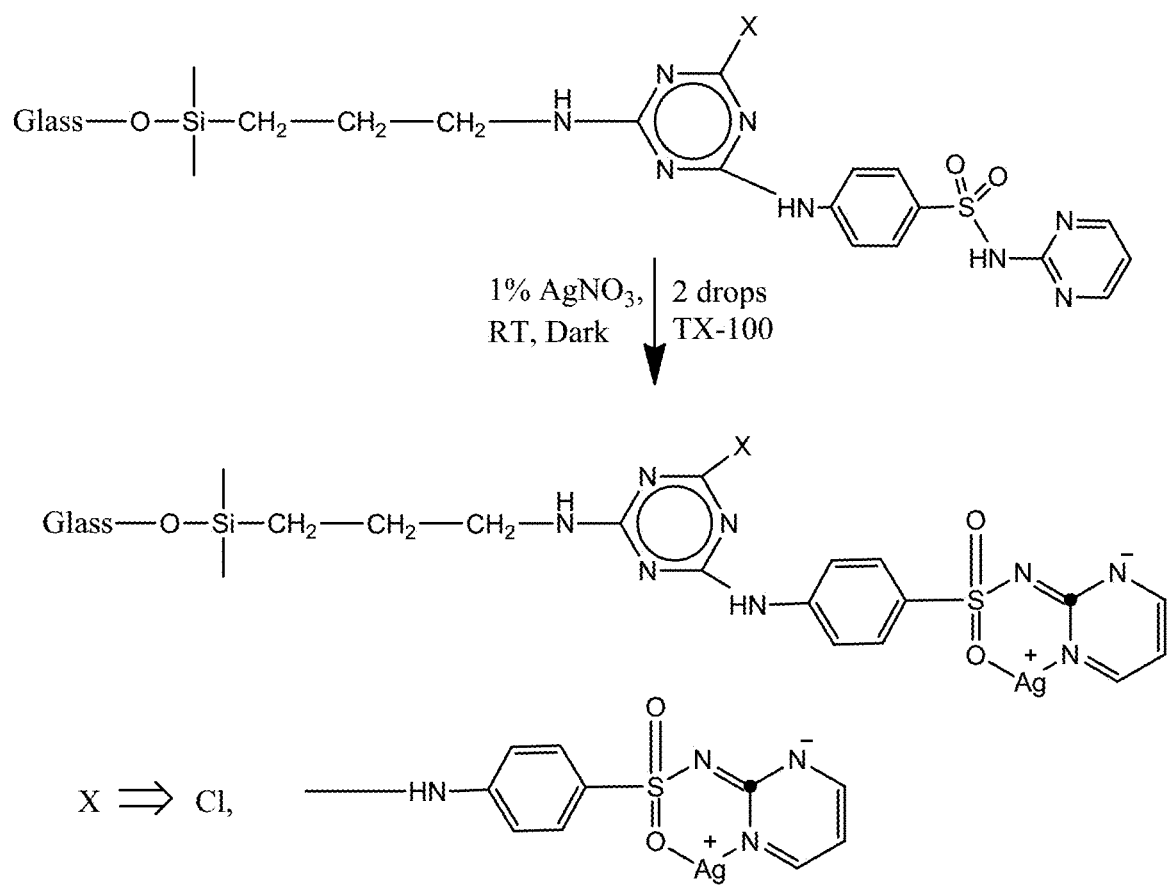
FIG. 6 is a reaction scheme for preparing a silver sulfadiazine-inorganic filler conjugate A-Glass-CyCl-SD-Ag according to principles of the invention.
Figure 7:
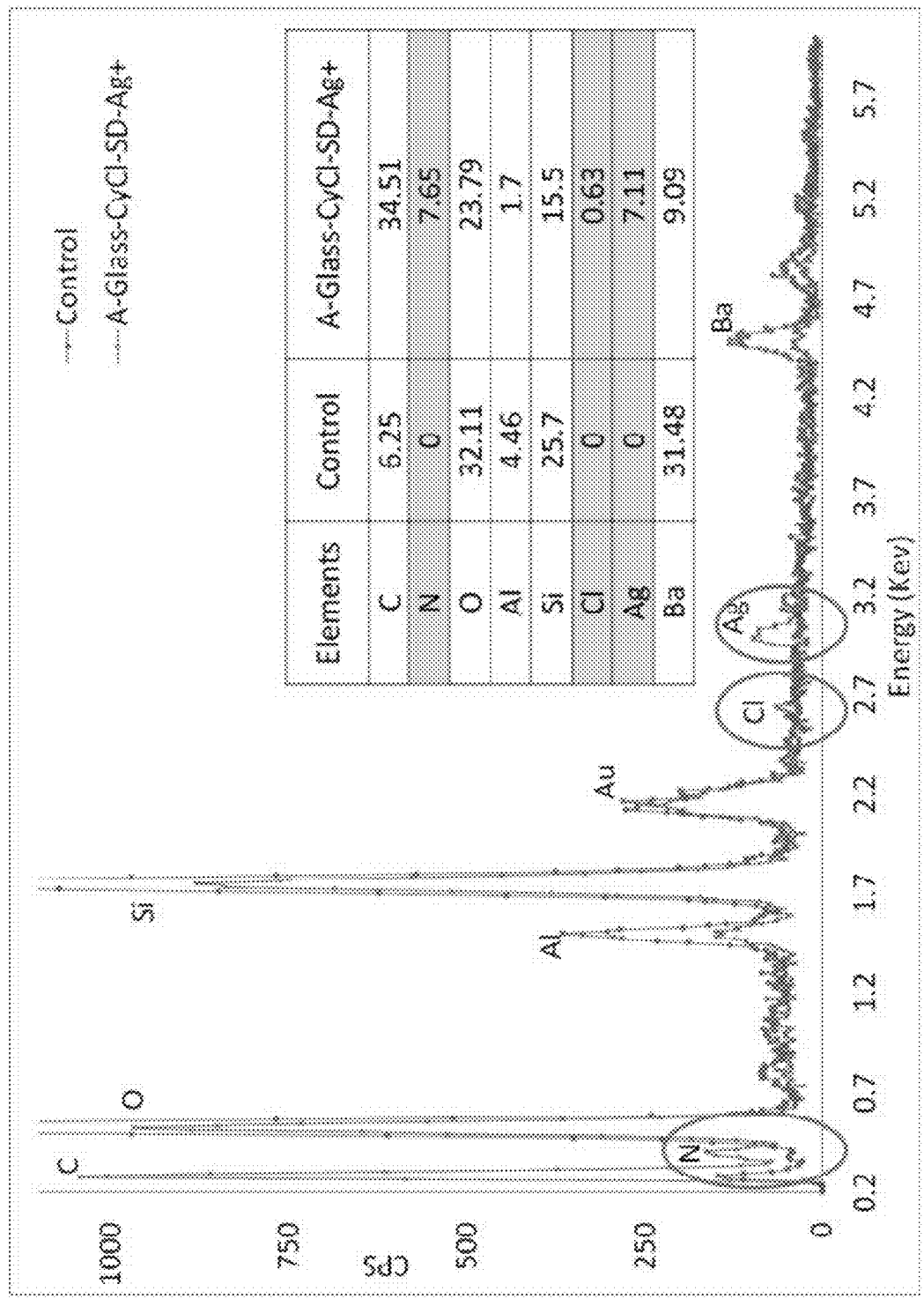
FIG. 7 is an SEM-EDS spectrum of A-Glass-CyCl-SD-Ag.

FIG. 6 is a reaction scheme for preparing a silver sulfadiazine-inorganic filler conjugate A-Glass-CyCl-SD-Ag The surface functionalization was confirmed by SEM-EDS and the results are shown in FIG. 7.

FIG. 7 is an SEM-EDS spectrum of A-Glass-CyCl-SD-Ag.

The silver content attached to modified glass powder was also confirmed by inductively coupled plasma atomic emission spectrometric analysis. This analysis was outsourced from an external laboratory.

Antimicrobial dental composites and/or dental adhesives are prepared. This is achieved by adding silver sulfadiazine-inorganic filler conjugates into the dental composites or dental adhesive formulations to replace the conventional inorganic fillers totally or partially, and follow the conventional preparation methods to produce antimicrobial dental composites and/or dental adhesives. These composites or adhesives that contain silver sulfadiazine-inorganic filler conjugates to produce antimicrobial functions have never been reported.

In the preparation of resin composite, 49.5% bis-glycidyl-methacrylate (bisGMA), 49.5% triethylene glycidyldimethacrylate (TEGDMA), 0.2% camphor quinone (CQ) and 0.8% 4-ethyl dimethylamino benzoate (4-EDMAB) were used as the resin parts (30% by weight), and glass powders were used as fillers (70% by weight). The control discs contained 100% of the original commercial glass to make up the 70% filler weight. For the antimicrobial discs, 2%, 5%, 10%, of the original glass was replaced by the silver glass powder (A-Glass-CyCl-SD-Ag).

The prepared composite mixture was placed in a custom made mold of 6.0 mm in diameter and 1.0 mm in height. A blue LED light at the wavelength 395-480 nm with 1000 $mW/cm^2$ of intensity was focused on the composite mixtures for 100 seconds to cure the resins.

After curing, the resin discs were used for the following antimicrobial tests. The bacteria, S. mutans, were grown and harvested following ATCC's recommendations. In a typical test, 2.5 µl bacteria solution with $10^6$-$10^7$ CFU of the bacteria were placed on a disc, which was covered by another identical disc to make a "sandwich". After 30 min of contact, the discs were placed in 1 ml PBS solution and vortexed for 60 seconds to wash out all the bacteria attached to the disks. The solution was serially diluted, and each dilution was placed on agar plates for incubation at 37° C. with 95% air and 5% $CO_2$ for 24 h. Colony forming units (CFUs) on the agar plates were counted. We found that from the control disc, as high as $10^6$ $CFU/cm^2$ of bacteria could be recovered. From the discs with 10% of the silver glass, no any bacteria could be recovered, demonstrating powerful antimicrobial effects.

It is believed that the non-leaching properties of the anti-microbial agents are novel. The antimicrobial agents are covalently bound onto fillers, and will not leach away.

In addition, the compositions described are expected to provide potent antimicrobial activity, be safe to use, and suffer no discoloration: Silver has potent antimicrobial effects and is safe to use. Thus, prior studies have used silver nano particles for dental applications. However, in the earlier applications, silver was easily oxidized and changed its appearance to a black color, which limited the acceptance of such materials as dental composites and dental adhesives. In the present invention, silver is bound onto the filler and forms coordination complexes with sulfadiazine. The resulting silver-sulfadiazine has the same efficacy and safety, yet it is white, and does not change to black. It is believed that this property will significantly improve the acceptance.

In the present invention, the antimicrobial agents are covalently bound onto conventional fillers. The appearance and handling characteristics of the resulting fillers will not be significantly altered. From the users' (dentists') point of view, no new monomers or new nano fillers are used, and they can still use the instruments and procedures they are most familiar with in their clinics. This ease of use (and use as a substitute material in presently available application/treatment methods) is believed to be a further help for the acceptance of the resulting products.

The compositions of the invention are believed to be useful in dental composites, dental adhesives, and other related applications. It is believed that the present invention provides a novel solution for a long-standing problem in dental (and possibly other medical) technology.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:
1. A composition of matter, comprising:
a particulate glass substrate modified as follows:
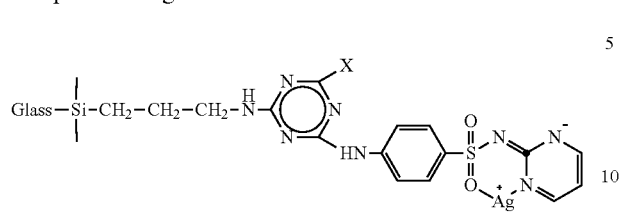
wherein X is
Cl or
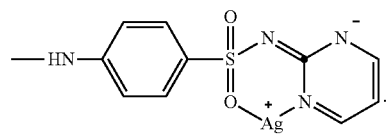
2. The composition of matter of claim 1, comprising
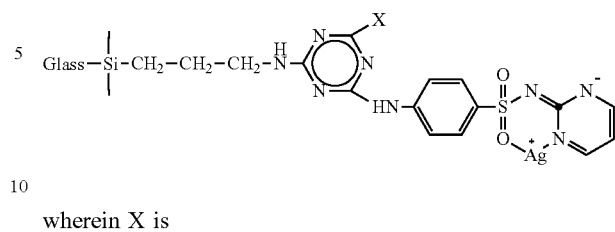
wherein X is
—HN—⌬—S(=O)(=O)—N=⌬—N⁻ ···Ag⁺
3. The composition of matter of claim 1, wherein said particulate glass substrate comprises a glass comprising BaO.
* * * * *